United States Patent [19]

Garabedian

[11] Patent Number: Plant 5,907

[45] Date of Patent: Mar. 17, 1987

[54] GRAPEVINE "GAR MUSCAT"

[76] Inventor: John M. Garabedian, 3104 E. Huntington Blvd., Fresno, Calif. 93702

[21] Appl. No.: 766,554

[22] Filed: Aug. 19, 1985

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Worrel & Worrel

[57] ABSTRACT

A grapevine particularly characterized by its grapes which are generally similar to those of the Muscat of Alexandria (unpatented) Grapevine, having the physical characteristics similar to the Muscat of Alexandria, but from which it is distinguished by a date of ripening which is 10 days to 2 weeks earlier than the Muscat of Alexandria and furthermore by producing clusters of grapes which are well-filled and neither compact nor straggling in appearance, as is characteristic of the Muscat of Alexandria variety.

1 Drawing Figure

BACKGROUND OF THE NEW VARIETY

The present invention relates to a new and distinct variety of grapevine to be known as the "Gar Muscat", and more particularly to a grapevine which is generally similar in physical characteristics to the Muscat of Alexandria Grapevine (unpatented), but from which it is distinguished in producing a berry which matures at least 10 days to 2 weeks earlier than the Muscat of Alexandria, is much more crisp than the Muscat of Alexandria, and whose clusters are well-filled, and not straggling in appearance, as is characteristic of the Muscat of Alexandria.

A substantial part of the applicant's professional life has been devoted to the creation of new and distinct varieties of fruit trees and vines. The present variety resulted from such efforts. The applicant has regularly selected grapevines having desired characteristics, and has cross-pollinated the selected grapevines, to try and produce progeny of improved characteristics. For example, in the creation of the instant variety of grapevine, an object of the present invention was to perpetuate the desirable characteristics of the Lebanese No. 9 variety of grapevine, (unpatented) and the Gar-Supreme Grapevine (unpatented).

ORIGIN AND ASEXUAL REPRODUCTION OF THE NEW VARIETY

The applicant cross-pollinated a selection from a Lebanese No. 9 grapevine as female, and a Gar-Supreme grapevine as a male, at a test plot located at the applicant's Ranch No. 1, located at 5841 East Kings Canyon Road, Fresno, County of Fresno, State of California, in 1974. The resultant progeny were grown to an extent sufficient to determine that their characteristics were as desirable. The subject variety was selected by the applicant for its characteristics and asexually reproduced by the applicant by cuttings that were rooted in 1978 and subsequently planted in 1979. The characteristics of the grapevines resulting from this asexual reproduction were identical to those of the original grapevine.

BRIEF DESCRIPTION OF THE DRAWING

The accompanying drawing is a color photograph of a bunch of grapes of the subject variety, a pair of characteristic leaves showing their dorsal and ventral coloration, and a typical section of the vine of the subject variety.

DETAILED DESCRIPTION

Referring more specifically to the pomological details of the new and distinct variety of grapevine, the following has been observed under the ecological conditions prevailing in the applicants' designated ranch near Fresno, Calif.

All major color code designations are by reference to the Munsell Limit Color Cascade. Common color names are also used in several instances.

VINE

Size: Medium.

Form: Horizontal, dense, tender.

Growth: Vigorous.

Productivity: Productive, the average vine producing 37 to 45 medium-sized clusters.

Trunk: Medium in size.

*Bark.*—Loose and shreddy in texture.

Canes: Long; variable; 162.56 cm. to 314.96 cm. (64 in. to 124 in.).

*Thickness.*—Slender.

*Color.*—Yellowish-Green to Brown.

*Shape.*—Straight.

Nodes: Angular in shape.

Internodes: Variable in length.

*Length.*—8.89 cm. to 16.51 cm. (3.5 in. to 6.5 in.).

Tendrils: Intermittent.

*Thickness.*—Slender; medium in length; smooth; trifurcated.

Internodes: Average in size.

*Length.*—12.60 cm. (4.96 in.).

Flowers: Fertile; having upright stamens and well-developed ovary.

*Date of bloom.*—February 1, through February 6; date of bloom is early as compared to other varieties of grapes.

LEAVES

SIZE: Medium to large.

*Length.*—11.75 cm. (4 to 6 inches).

*Width.*—17.65 cm. (6.95 inches).

*Thickness.*—Thin.

*Shape.*—Roundish.
*Petiole length.*—9.65 cm. (3.8 inches)
*Color.*—Ventral Surface — Dark Green (MCC 19-14 through 20-14); Dorsal Surface — A somewhat lighter and dull shade of green (MCC 23-21 through 24-13).
*Leaf texture.*—Smooth and glossy, globular.
*Lobes.*—Variable from 3 to 5 with a majority of leaves showing 3 distinct lobes.
*Terminal lobe.*—Obtuse.
*Petiolar sinus.*—Deep; medium in width; V- or U-shaped.
*Basal sinus.*—Shallow in depth; medium in width.
*Lateral sinus.*—Shallow in depth, although occasionally there may be no distinct sinus; narrow in width.
*Margin.*—Serrate.
*Teeth.*—Medium in depth; narrow in width.

FRUIT

Maturity when described: Approximately the same time as the Thompson Seedless (unpatented), i.e. the first week of August; ripening date is average as compared to other varieties.
Keeping quality: Unknown at the present time.
Shipping quality: Marginal, the berries separate readily from the pedicel.
Cluster:
*Size.*—Medium to large; medium in length; broad; tapering; single; regular; medium in density.
*General appearance.*—Short, conical, with a broad base well filled, and not "straggling" in appearance.
Peduncle: Short in length, medium in thickness.
Pedicle: Short in length, slender in thickness.
*Warts.*—very few.
Brush: Not present; the berries separate cleanly from the pedicle.
Berry:

*Size.*—Medium to large; variable; oblate generally; average length 24.6 mm.; average width 19.7 mm.
*Color.*—Light Yellow (MCC 23-9 through 24-10).
*Weight.*—Variable from 4.2 to 4.7 grams.
Skin:
*Thickness.*—Thin.
*Texture.*—Tender.
*Adherence to the pulp.*—Adherent.
Flesh:
*Color.*—Greenish-White.
*Texture.*—Soft and crisp; juicy, sweet, subacid and spicy.
Quality: Good to excellent.
Seeds:
*Numbers of seeds.*—Variable from 1 to 4 per berry.
*Size.*—Variable.
*Texture of seeds.*—Soft in texture.
*Color.*—Variable from Yellowish-Brown to Brown.
Use: Fresh.

Although the new variety of grapevine possesses the described characteristics as a result of the growing conditions prevailing in the San Joaquin Valley of Central California, it is to be understood that variations of the usual magnitude in characteristics incident to growing conditions, fertilization, pruning and pest control are to be expected.

Having thus described and illustrated my new variety of grapevine, I claim:

1. A new and distinct variety of grapevine to be known as the "Gar Muscat", substantially as illustrated and described, characterized principally by its production of grapes which mature approximately 10 days to 2 weeks earlier than the Muscat of Alexandria Grapevine, which it most nearly resembles, but from which it is distinguished by clusters that are well-filled, neither compact nor straggling in appearance.

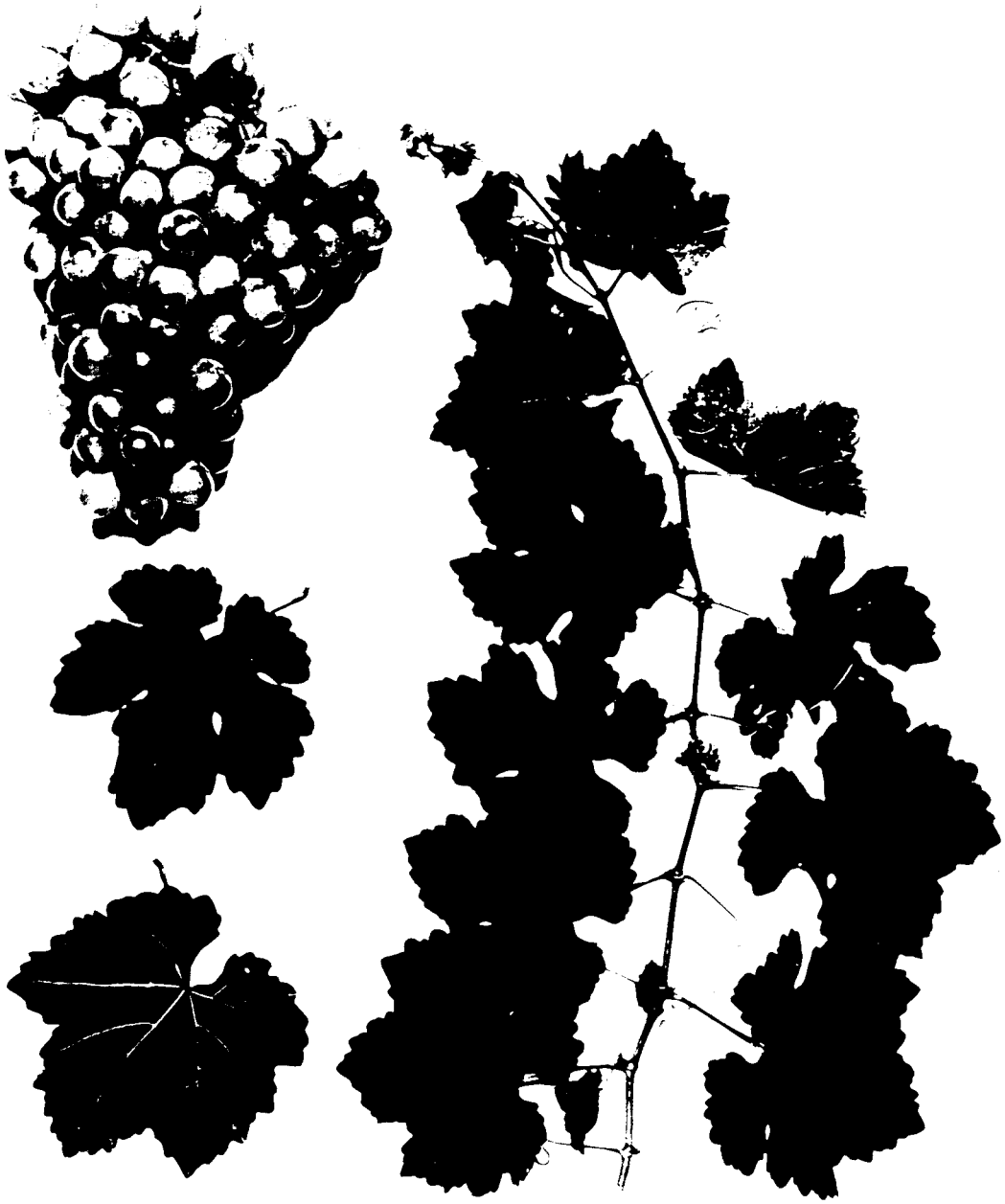

* * * * *